United States Patent [19]

Jackson et al.

[11] 4,218,389

[45] Aug. 19, 1980

[54] PROCESS FOR MAKING METHANOL

[75] Inventors: Robert G. Jackson; Richard M. Tillman, both of Ponca City, Okla.

[73] Assignee: Conoco, Inc., Ponca City, Okla.

[21] Appl. No.: 763,395

[22] Filed: Jan. 28, 1977

[51] Int. Cl.$^2$ .............................................. C07C 31/06
[52] U.S. Cl. ..................................... 260/449.5; 55/57
[58] Field of Search ........................... 260/449.5; 55/57

[56] References Cited

U.S. PATENT DOCUMENTS

| | | | |
|---|---|---|---|
| 1,788,170 | 1/1931 | Pier et al. | 260/449.5 |
| 2,873,814 | 2/1959 | Maher | 55/57 X |
| 2,928,885 | 3/1960 | Newsome | 55/57 X |
| 3,920,717 | 11/1975 | Marion | 260/449.5 |
| 3,940,428 | 2/1976 | Connell et al. | 260/449.5 |
| 3,972,958 | 8/1976 | Garwood et al. | 260/449.5 |

OTHER PUBLICATIONS

Kirk-Othmer, Encyclopedia of Chemical Technology, vol. 5, pp. 671-672, vol. 13, 381-383, 1964.

*Primary Examiner*—Howard T. Mars
*Attorney, Agent, or Firm*—Richard W. Collins

[57] ABSTRACT

A process for producing methanol from air-blown gasified coal. A feed gas stream obtained by the coal gasification step is combined with a recycle gas stream and fed to a reactor where carbon oxides are converted to methanol. Exit gas from the reactor is scrubbed to remove carbon monoxide, and the carbon monoxide-free exit gas is then chilled to remove all components except hydrogen. The hydrogen is then combined with the carbon monoxide and used as a recycle stream. The process enables use of an air-blown gasified coal stream while maintaining the nitrogen content in the reactor at an acceptably low level.

6 Claims, 1 Drawing Figure

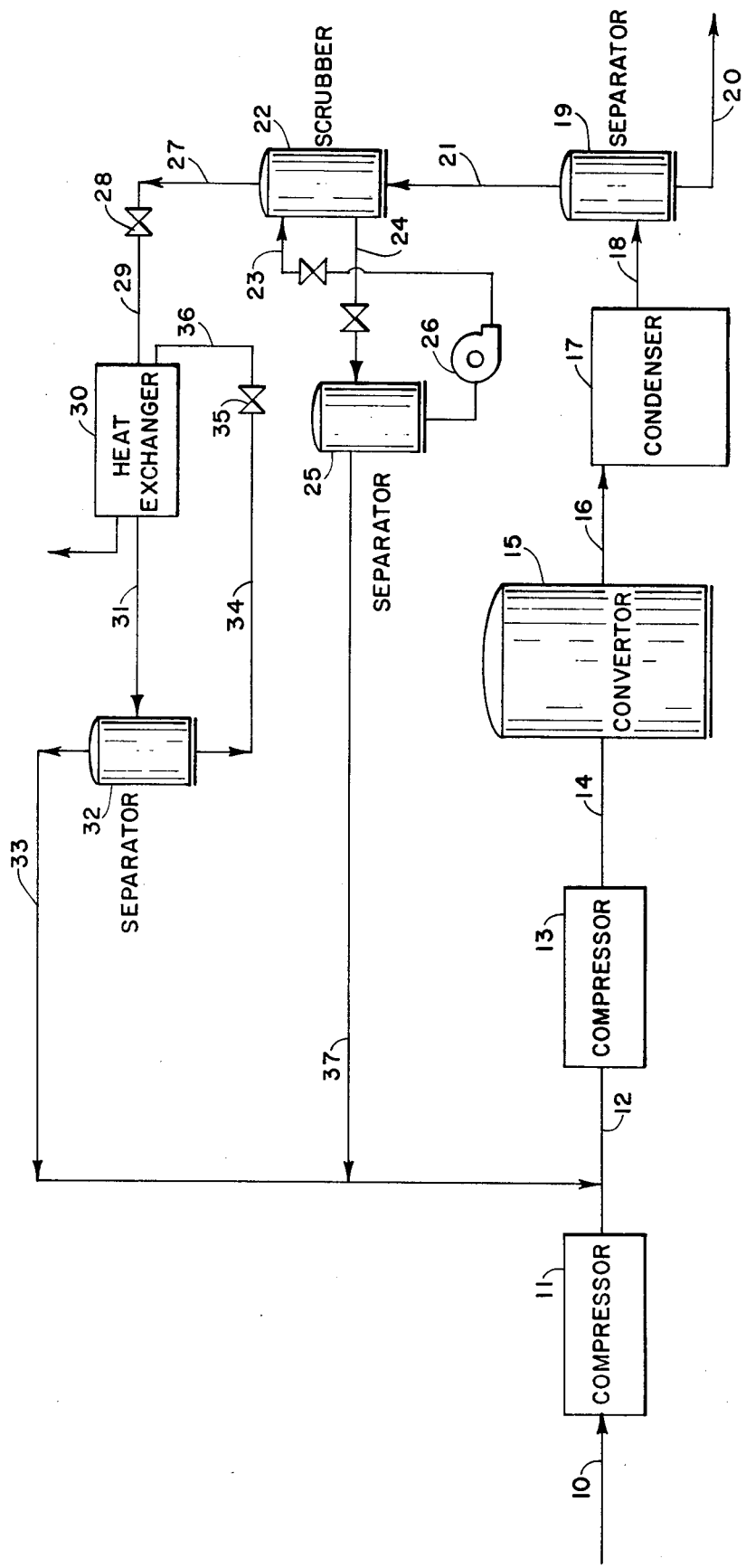

PROCESS FOR MAKING METHANOL

BACKGROUND OF THE INVENTION

1. Field of the Invention

This invention relates to production of methanol from solid carbonaceous material such as oil shale, coal and the like. More particularly, the invention relates to production of methanol utilizing a feed gas obtained by air-blowing coal. The feed gas contains carbon oxides which are converted to methanol by catalytic hydrogenation.

Most coal gasification processes utilize an oxygen-blown gasifier. The amount of oxygen required for this process is large, and accordingly a costly air separation plant is necessary.

Air-blown gasifiers, not requiring an air separation plant, are available, but the gas from air-blown gasifiers has a high (about 50 volume percent) nitrogen content. Reactors for making methanol from gas obtained from coal gasifiers generally do not operate efficiently if the feed gas has a nitrogen content above about 25 volume percent. For this reason, feed gas from air-blown gasifiers has not been successfully used to produce methanol.

2. Description of the Prior Art

U.S. Pat. No. 1,788,170 describes a process for producing methanol using feed gas which is apparently from an air-blown gasifier. However, no provision is made in the reference process for reducing the nitrogen content to the reactor.

British Pat. No. 266,405 discloses the formation of methanol by catalytic conversion of a feed gas made by coal gasification with air so that the feed gas contains about 50 percent nitrogen. The reference further discloses removal of a portion of the gas from the conversion loop to adjust the composition of the gas stream.

SUMMARY OF THE INVENTION

According to the present invention, methanol is produced using feed gas from an air-blown coal gasifier by catalyzed reaction with hydrogen in a reactor. The feed gas from the air-blown gasifier contains a high amount of nitrogen, and the conversion reaction does not proceed efficiently in the presence of more than about 25 volume percent nitrogen. Removal of nitrogen from the feed gas is not practical, so a low-nitrogen recycle gas stream is utilized to effectively lower the nitrogen ratio in the reactor. Methanol from the reactor is condensed and recovered, and the methanol-free exit gas from the reactor is then processed to obtain a relatively nitrogen-free recycle gas stream.

In accordance with an essential feature of the invention, carbon monoxide is scrubbed from the reactor exit gas after the methanol has been recovered. The scrubbed carbon monoxide is then recovered for use as part of the recycle gas stream. The carbon monoxide-free exit gas stream is further processed to remove all of the higher-boiling components, thus providing a stream which is essentially hydrogen for reuse in the process. This hydrogen is combined with the carbon monoxide and used as recycle gas to the reactor. By using a high enough ratio of recycle gas to high-nitrogen feed gas, the nitrogen content of gas to the reactor can be maintained well below 25 percent. It is necessary for efficient operation of the reactor that the nitrogen content be maintained below about 25 percent.

It is therefore an object of the invention to provide an improved process for producing methanol.

It is a further object to provide such a process which can utilize a feed gas from an air-blown coal gasifier.

BRIEF DESCRIPTION OF THE DRAWINGS

The FIGURE is a schematic flow diagram illustrating the process of the invention.

DESCRIPTION OF THE PREFERRED EMBODIMENT

The most preferred embodiment of the invention will now be described broadly with reference to the drawing.

A feed gas stream from an air-blown gasifier in which coal is reacted with steam to produce a stream comprising about one-half nitrogen, about one-third hydrogen, and the balance carbon oxides with a small amount of methane is passed from feed line 10 to compressor 11 and out of compressor 11 through intermediate line 12 at a pressure of about 700 lbs/inch$^2$. The feed gas from line 12 passes to a second compressor 13 where it is compressed to about 1500 lbs/inch$^2$. The compressed feed gas then passes through line 14 to reactor 15 where the carbon oxides are catalytically hydrogenated to produce a product stream including methanol. The product from reactor 15 passes through line 16 to condensor 17 where a crude methanol product is condensed. The methanol product and uncondensed gases then pass through line 18 to separator 19 and a liquid product comprising crude methanol is withdrawn through product line 20.

Uncondensed gases from separator 19 pass through line 21 to carbon monoxide scrubber 22 which removes the carbon monoxide from the gas stream. A preferred scrubbing solution is an aqueous copper ammonium salt solution which enters scrubber 22 through line 23 and is withdrawn from scrubber 22 through line 24. The scrubbing solution and absorbed carbon monoxide are then passed to separator 25 at a pressure of about 700 lbs/inch$^2$ where carbon monoxide separates from the scrubbing solution. Lean scrubbing solution from separator 25 is then recycled to scrubber 22 through pump 26.

Carbon monoxide-free gas from scrubber 22 then passes through line 27 to expansion valve 28 where the pressure is reduced to about 700 lbs/inch$^2$, reducing the temperature of the gas stream prior to passing it from line 29 to heat exchanger 30 where the gas is then further cooled until the higher boiling gases condense. Nitrogen, methane and carbon dioxide are condensed in heat exchanger 30 and passed along with uncondensed hydrogen through line 31 to separator 32. Uncondensed hydrogen passes from separator 32 through line 33. The condensed liquids from separator 32 are removed through line 34 and passed through expansion valve 35 and then through line 36 in heat exchange relation through heat exchanger 30 to provide cooling for the gases from expansion valve 28. If necessary, supplemental refrigeration may be utilized to obtain the necessary separation of hydrogen from the gas stream passing through heat exchanger 30. The gas from line 33, principally hydrogen, is combined with carbon monoxide from separator 19 and line 37 and then combined with the feed gas in line 12. The recycled hydrogen and carbon monoxide improve the efficiency of the process by providing carbon monoxide to reactor 15 and by providing a diluent effect on the feed gas stream such that the nitrogen content of the feed gas to reactor 15 can be maintained well below 25 percent by volume. It is recognized that the conversion reaction in reactor 15 proceeds inefficiently if the nitrogen content in the feed gas is higher than about 25 percent by volume, and preferably the recycle ratio is high enough to keep the nitrogen content below about 15 percent in the reactor.

The process described broadly above enables the production of methanol from a feed gas obtained by air blowing coal even though the nitrogen content of the feed gas from the gasifier is much too high for efficient conversion to methanol.

The process makes it possible to produce methanol from coal without requiring an oxygen-blown gasifier which in turn requires an expensive air separation plant.

Air-blown gasifiers are available commercially, as are reactors of the type used to catalytically hydrogenate carbon oxides in the conversion reaction utilized by this invention. All of the equipment required to carry out the process is conventional processing equipment available commercially, and can be readily selected by one skilled in the art.

The following example illustrates the process of the invention on a commercial scale utilizing presently-available equipment.

EXAMPLE I 430 tons of coal per hour is gasified in an air-blown gasifier to produce a feed gas stream after cleanup comprising 32 million standard cubic feet per hour (MMSCFH) of gas having a composition of about 49 percent nitrogen, 33 percent hydrogen, 12 percent carbon monoxide, 4 percent carbon dioxide and 2 percent methane. This feed gas, at a pressure of 365 lbs/inch$^2$, is compressed to 700 lbs/inch$^2$ and combined with a recycle gas obtained in a manner to be described in detail below, and then further compressed to about 1500 lbs/inch$^2$. The compressed feed gas including the combined recycle gas is then introduced to a reactor where it is catalytically converted to produce methanol from the carbon oxides and hydrogen. The product gas from the reactor is then condensed and about 6,000 tons per day of crude methanol containing about 18 percent water is withdrawn from a product separator. Uncondensed gases from the reactor are scrubbed with aqueous copper ammonium salt solution to remove carbon monoxide, and the uncondensed gases are then expanded and chilled to condense essentially all of the components except hydrogen therefrom. The carbon monoxide scrubbed from the exit gas is separated from the scrubbing solution and utilized as a part of the recycle gas. About 1.8 MMSCFH of 95 percent carbon monoxide at 700 lbs/inch$^2$ is recovered in this manner. About 82 MMSCFH of uncondensed gas comprising about 95 percent hydrogen at 700 psi is combined with the carbon monoxide, and the predominantly hydrogen and carbon monoxide stream is then utilized as recycle gas, providing a diluent effect on the feed gas, which contains about 49 percent nitrogen, such that the nitrogen content in the reactor is below 15 percent by volume. The crude methanol product can be purified by conventional procedures if desired.

The process of the invention is also suitable for processing gases from an in situ partial combustion of coal or oil shale. Normally, an in situ partial combustion of coal is designed to produce a low BTU gas by injecting air down an injection well into a coal deposit, igniting the coal, and recovering combustion gases from a separate recovery well or wells. These combustion gases normally are used for production of electricity. The following example describes the use of the process of the invention using combustion gases from an in situ combustion process as feed.

EXAMPLE II

Combustion gas from an in situ partial combustion of coal process is processed and utilized as feed to a methanol convertor. This combustion gas containing about 13 percent carbon dioxide, 13.5 carbon monoxide, 12 percent hydrogen, 4.5 percent methane and 57 percent nitrogen is fed to a shift reactor to convert carbon monoxide and water to hydrogen and carbon dioxide. The shift reactor gas is scrubbed to remove excess carbon dioxide to provide a gas consisting of about 2 percent carbon dioxide, 7.5 percent carbon monoxide, 21 percent hydrogen, 5 percent methane and 64 percent nitrogen. This gas is then processed as in Example I except that the recycle ratio is maintained at a rate to produce a nitrogen content in the reactor of about 20 percent.

It will be appreciated that numerous variations and modifications to the process as described in detail above could be made without departing from the invention. For example, the particular process conditions such as pressure, temperature, recycle ratio, etc. can be varied to suit the circumstances. The exact compositions and volumes of the recycle hydrogen and carbon monoxide streams can be varied within a considerable range to best suit the particular situation.

What is claimed is:

1. A process for producing methanol from solid carbonaceous material comprising:
    subjecting said carbonaceous material to an air-blown gasification step to produce a feed gas stream comprising nitrogen, hydrogen, carbon monoxide, carbon dioxide and methane;
    reacting said feed gas stream in a reactor to produce an effluent gas stream containing methanol;
    condensing methanol from said effluent gas stream and withdrawing condensed methanol therefrom;
    scrubbing carbon monoxide from said effluent gas stream;
    condensing the higher boiling components from said effluent gas stream after carbon monoxide scrubbing to produce a recycle gas stream which is predominantly hydrogen;
    combining said predominantly hydrogen recycle gas stream with carbon monoxide previously scrubbed from said effluent gas stream;
    combining said recycle gas stream including carbon monoxide with said feed gas stream to provide a combined feed gas stream and recycle gas stream including recycle carbon monoxide for introduction to said reactor, said combined feed gas stream and recycle gas stream having a nitrogen content of less than 25 volume percent; and
    introducing said combined feed gas stream and recycle gas stream into said reactor.

2. The process of claim 1 wherein said feed gas stream is about 50 percent nitrogen by volume.

3. The process of claim 1 wherein the combined feed gas stream and recycle gas stream including recycled carbon monoxide has a nitrogen content of not more than 15 volume percent.

4. The process of claim 1 wherein carbon monoxide is scrubbed from said effluent gas stream utilizing an aqueous copper ammonium salt solution.

5. The process of claim 1 wherein said higher boiling components of said effluent gas stream are condensed utilizing cooling provided by expansion of said effluent gas stream.

6. The process of claim 1 wherein said carbonaceous material is coal.

* * * * *